(12) United States Patent
Ogata et al.

(10) Patent No.: US 12,059,544 B2
(45) Date of Patent: Aug. 13, 2024

(54) METHOD AND DEVICE FOR ENHANCED COMPOSITION DELIVERY

(71) Applicant: ASAHI MEDICAL TECHNOLOGIES, INC., Pleasanton, CA (US)

(72) Inventors: Wayne Ogata, San Ramon, CA (US); Xiang Ian Gu, Foster City, CA (US); Steven Meyer, Oakland, CA (US)

(73) Assignee: ASAHI MEDICAL TECHNOLOGIES, INC., Pleasanton, CA (US)

( * ) Notice: Subject to any disclaimer, the term of this patent is extended or adjusted under 35 U.S.C. 154(b) by 0 days.

(21) Appl. No.: 18/224,395

(22) Filed: Jul. 20, 2023

(65) Prior Publication Data

US 2023/0355941 A1    Nov. 9, 2023

Related U.S. Application Data

(62) Division of application No. 16/343,699, filed as application No. PCT/US2017/057650 on Oct. 20, 2017, now Pat. No. 11,857,748.
(Continued)

(51) Int. Cl.
*A61M 37/00* (2006.01)
*A61B 17/22* (2006.01)
(Continued)

(52) U.S. Cl.
CPC ............. *A61M 37/00* (2013.01); *A61B 17/22* (2013.01); *A61N 1/306* (2013.01); *A61N 1/40* (2013.01);
(Continued)

(58) Field of Classification Search
CPC .......... A61M 37/00; A61M 2037/0007; A61M 25/104; A61M 2025/0057;
(Continued)

(56) References Cited

U.S. PATENT DOCUMENTS 2,248,934 A * 7/1941 Auzin ............... A61M 25/1027
264/250
4,955,377 A * 9/1990 Lennox ................... A61B 18/08
607/105

(Continued)

FOREIGN PATENT DOCUMENTS

JP      10-230017 A      9/1998
JP      2009-502806 A    7/2006
(Continued)

OTHER PUBLICATIONS

Office Action from Japanese Application No. 2023-146728 dated Dec. 11, 2023.

*Primary Examiner* — Nilay J Shah
(74) *Attorney, Agent, or Firm* — Troutman Pepper Hamilton Sanders LLP (Rochester)

(57) ABSTRACT

Methods and devices that provide enhanced delivery of a composition to a body region of a patient utilizing radiofrequency energy include directing a first electrode and a second electrode coupled to a radiofrequency energy source to a location proximate to the body region. Radiofrequency energy is provided in modulated pulses from the radiofrequency energy source to the body region from at least one of the first electrode and the second electrode to provide a delivery condition configured to enhance delivery of the composition. The composition is delivered proximate to the body region using a composition delivery element. Devices for enhance composition delivery are also disclosed.

6 Claims, 7 Drawing Sheets

Related U.S. Application Data

(60) Provisional application No. 62/410,685, filed on Oct. 20, 2016.

(51) Int. Cl.
| | | |
|---|---|---|
| *A61N 1/30* | (2006.01) | |
| *A61N 1/40* | (2006.01) | |
| *A61N 1/44* | (2006.01) | |
| *A61B 18/00* | (2006.01) | |
| *A61B 18/14* | (2006.01) | |
| *A61K 9/00* | (2006.01) | |
| *A61M 25/00* | (2006.01) | |
| *A61M 25/10* | (2013.01) | |
| *A61N 1/32* | (2006.01) | |

(52) U.S. Cl.
CPC ...... *A61N 1/44* (2013.01); *A61B 2017/22001* (2013.01); *A61B 2017/22005* (2013.01); *A61B 2017/22084* (2013.01); *A61B 2018/0022* (2013.01); *A61B 18/14* (2013.01); *A61K 9/0009* (2013.01); *A61M 2025/0057* (2013.01); *A61M 25/104* (2013.01); *A61M 2025/105* (2013.01); *A61M 2037/0007* (2013.01); *A61N 1/327* (2013.01)

(58) Field of Classification Search
CPC .......... A61M 2025/105; A61M 5/1723; A61M 2005/1726; A61N 1/40; A61B 18/14; A61B 2017/22001; A61B 2018/0022
See application file for complete search history.

(56) References Cited

U.S. PATENT DOCUMENTS

| | | | | |
|---|---|---|---|---|
| 5,106,360 A | * | 4/1992 | Ishiwara | A61N 5/1002 600/3 |
| 5,304,121 A | * | 4/1994 | Sahatjian | A61L 29/16 606/194 |
| 5,439,446 A | * | 8/1995 | Barry | A61M 25/104 604/103.01 |
| 2002/0077592 A1 | * | 6/2002 | Barry | A61F 2/958 623/1.42 |
| 2003/0114791 A1 | * | 6/2003 | Rosenthal | A61L 29/085 604/21 |
| 2007/0112344 A1 | * | 5/2007 | Keilman | A61B 5/0031 606/41 |
| 2008/0300610 A1 | | 12/2008 | Chambers | |

FOREIGN PATENT DOCUMENTS

| | | | | |
|---|---|---|---|---|
| WO | WO-9741916 A1 | * | 11/1997 | ............ A61F 2/958 |
| WO | 0056237 A2 | | 9/2000 | |
| WO | 2007014003 A2 | | 2/2007 | |

\* cited by examiner

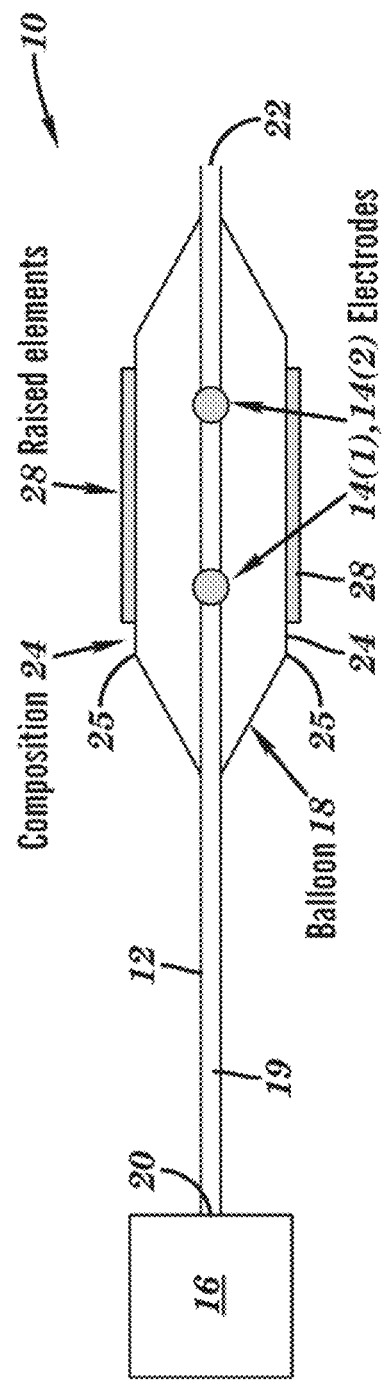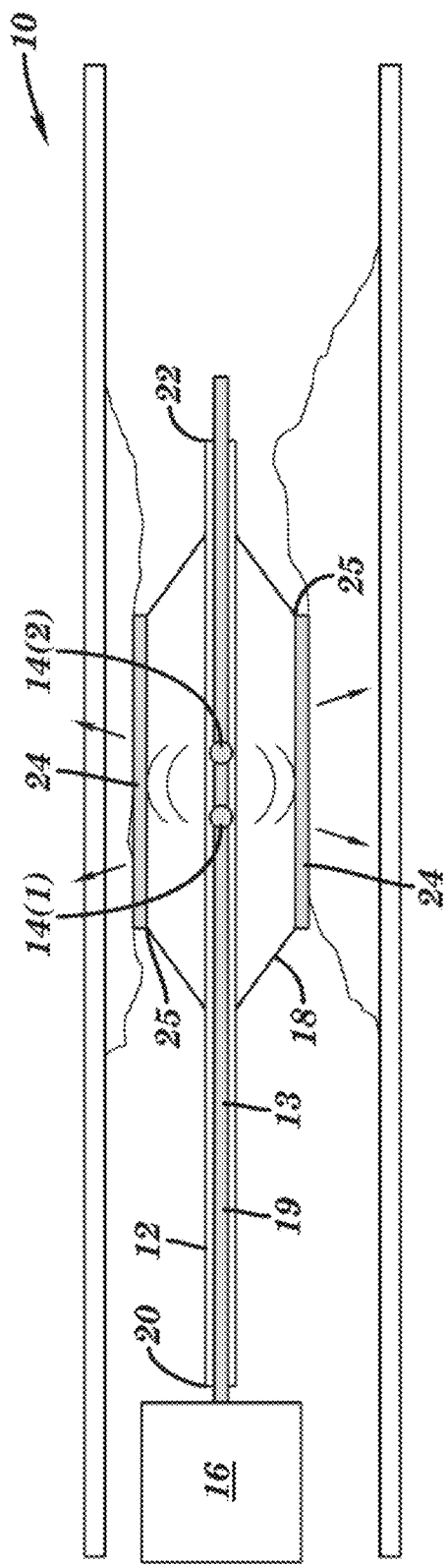

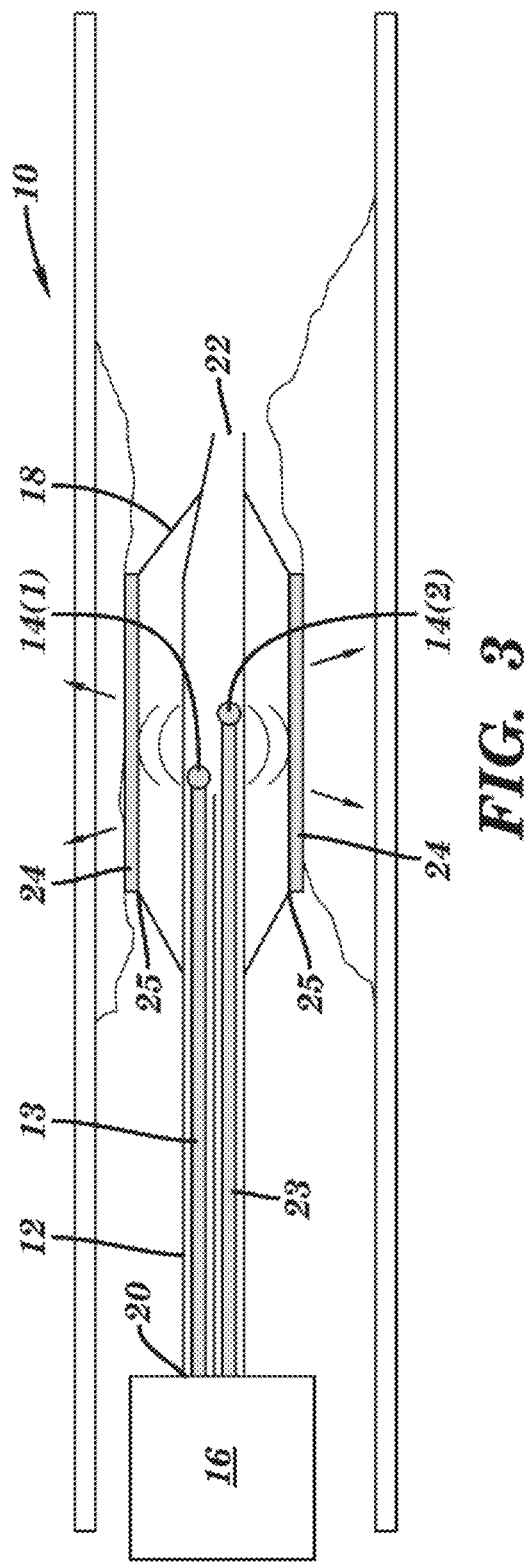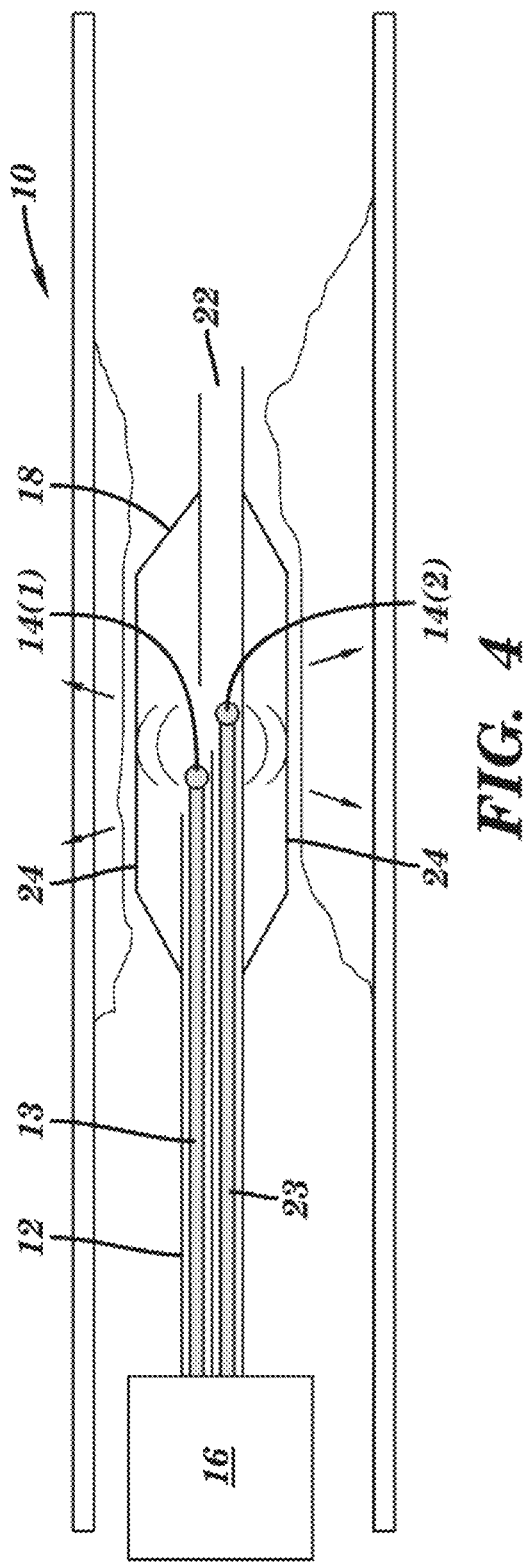

METHOD AND DEVICE FOR ENHANCED COMPOSITION DELIVERY

This application is a divisional of U.S. patent application Ser. No. 16/343,699, filed Apr. 19, 2019, which is a national stage application under U.S.C. § 371 of PCT International Application Serial No. PCT/US2017/057650, filed Oct. 26, 2017, and which claims priority benefit of U.S. Provisional Patent Application Ser. No. 62/410,685, filed on Oct. 20, 2016, which are hereby incorporated by reference in their entirety.

FIELD

The present invention relates to a method and device for enhanced composition delivery.

BACKGROUND

Current methods and devices for treating occlusions in the body (blood vessel or grafts) employ the use of balloon catheters or stents to deliver drugs to the inside of the blood vessel. Drug eluting stents provide the advantage that the device can be designed to prolong delivery of the drug for several weeks or several months by altering the drugs elution profile, but in most cases leave behind a metallic scaffold. Drug coated balloons provide the advantage of not leaving anything behind, however the drug is delivered for a shorter period of time due to the fact that the vessel is occluded by the balloon while the drug is being delivered.

In both devices, the primary mechanism of delivery is simple diffusion of the drug into the vessel wall and is subject to washout of the drug while under flow conditions. Moreover, since simple diffusion is the primary mechanism of delivery, in both devices the drug is delivered superficially onto the vessel wall.

SUMMARY

A method for enhanced delivery of a composition to a body region of a patient utilizing radiofrequency energy includes directing a first electrode and a second electrode coupled to a radiofrequency energy source to a location proximate to the body region. Radiofrequency energy is provided in modulated pulses from the radiofrequency energy source to the body region from at least one of the first electrode and the second electrode to provide a delivery condition configured to enhance delivery of the composition. The composition is delivered proximate to the body region using a composition delivery element.

A device for enhanced delivery of a composition to a body region of a patient utilizing radiofrequency energy includes a first longitudinal member with a proximal end and a distal end with at least one lumen extending between the proximal end and the distal end. A composition delivery element is located at the distal end of the longitudinal member. The composition delivery element has the composition coated on an outside surface thereof. At least two electrodes are coupled to a radiofrequency source and located within the composition delivery element. The electrodes are insulated such that at least two electrodes are capable of generating an electric field to enhance delivery of the composition to the body region.

This technology provides a number of advantages including providing more efficient and effective devices and methods for delivering a composition to a body region. The devices and methods of this technology allow the composition to remain within the body region site for an extended period of time to provide enhanced treatment. In particular, the use of cavitation, shockwaves, electroporation, or the like, generated by radiofrequency energy or other energy source aids in the delivery of the composition. The present technology advantageously provides an enhanced method for delivering the drug into the vessel wall or occlusion such that the drug remains within the targeted site for a longer period of time without leaving anything behind. Prolonged action of the drug within the targeted site can lead to improved outcomes (e.g. reduced reocclusion, restenosis, or revascularization rates).

BRIEF DESCRIPTION OF THE DRAWINGS

FIG. 1 is a schematic of an exemplary device for composition delivery using radiofrequency energy of the present technology.

FIG. 2 is a schematic of another exemplary device for composition delivery using radiofrequency energy of the present technology located in a body region having an occlusion.

FIG. 3 is a schematic of a further exemplary device for composition delivery using radiofrequency energy of the present technology located in a body region having an occlusion.

FIG. 4 is a schematic of an alternative example of the device for composition delivery shown in FIG. 3.

DETAILED DESCRIPTION

Figure 5:
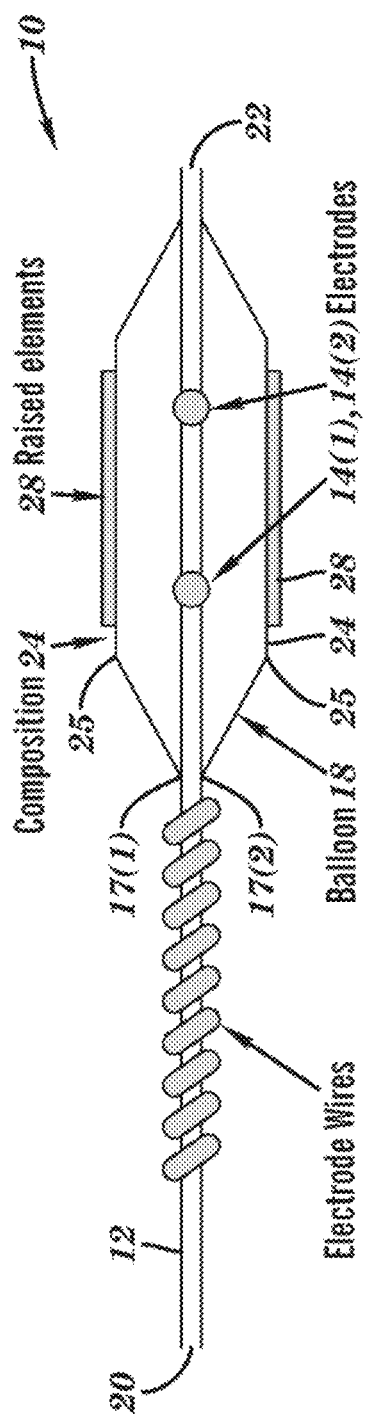
FIG. 5 is a schematic of the exemplary device for composition delivery using radiofrequency energy shown in FIG. 1 illustrating an exemplary coupling between the electrodes and the radiofrequency energy source.

An exemplary composition delivery device 10 for enhanced delivery of a composition to a body region of a patient utilizing radiofrequency energy is illustrated in FIGS. 1 and 5. Although radiofrequency energy is described, other energy modalities, such as ultrasound or laser energy by way of example, may be utilized. The composition delivery device 10 includes a first longitudinal member 12 including electrodes 14(1) and 14(2), a radiofrequency energy source 16, and a composition delivery element 18, although the composition delivery device 10 could include other types and/or numbers of elements, components, and/or devices in other configurations, such as additional electrodes and/or longitudinal members. This exemplary technology provides a number of advantages including providing more efficient and effective composition delivery to a region within the body of a patient.

Referring more specifically to FIG. 1, the composition delivery device 10 includes a first longitudinal member 12 that is configured to be advanced into the body of a patient and located near a body region of the patient. The body region may be various regions in the body, including organs, body lumens or cavities, such as various ducts or vessels, blood vessels, grafts, glands. In one example, the body region may be an area in the body including an occlusion or a tumor that requires treatment. In this example, the first longitudinal member 12 includes a lumen 19 extending between a proximal end 20 and a distal end 22 of the first longitudinal member 12, although the longitudinal member 12 may include additional lumens. The lumen 19 is configured to receive additional longitudinal members therein, such as guidewires, catheters, microcatheters, or probes, by way of example only.

In this example, the longitudinal member 12 has electrodes 14(1) and 14(2) located thereon to provide a bipolar arrangement of the electrodes 14(1) and 14(2), although the electrodes 14(1) and 14(2) may be located on other elements in other configurations to provide a bipolar arrangement.

In another example, as shown in FIG. 2, the composition delivery device 10 further includes a second longitudinal member 13 that is configured to be inserted into the lumen 19 of the first longitudinal member 12 to be delivered proximate to the body region of the patient. In this example, the second longitudinal member 13 is a guidewire or a catheter with the electrodes 14(1) and 14(2) located thereon to provide the bipolar arrangement.

In yet another example, as shown in FIG. 3, the composition delivery device 10 further includes a third longitudinal member 23 that is configured to be inserted into the lumen 19 of the first longitudinal member. The third longitudinal member 23 may be a guidewire or a catheter, by way of example only. The second longitudinal member 13 and the third longitudinal member 23, which are independent, non-overlapping guidewires or catheters, may be delivered to the body region in the same direction or in opposition directions as described below.

In a further example, one of the electrodes 14(1) or 14(2) is located on a patch that may be placed on the patient's skin proximate the body region of the patient to be treated. The patch is placed in close proximity to the body region to allow for the bipolar arrangement between the electrodes 14(1) and 14(2).

Referring now to FIG. 4, in one example the lumen 19 of the first longitudinal member 12 includes multiple lumen sections to deliver the second longitudinal member 13 and the third longitudinal member 23 separately to the body region. In yet another example, the second longitudinal member 13 may be configured to receive the third longitudinal member 23 such that the third longitudinal member 23 is located within the second longitudinal member 13. Referring again to FIG. 3, in this example the electrodes 14(1) and 14(2) are located on the second longitudinal member 13 and the third longitudinal member 23, respectively, in order to provide the bipolar arrangement.

In one example, the electrodes 14(1) and 14(2) may be balloon markers, although other types of electrodes may be utilized. Referring to FIG. 5, the electrodes 14(1) and 14(2) are coupled to the radiofrequency energy source 16 via wires 17(1) and 17(2). The wires 17(1) and 17(2) are wrapped in a helical configuration about the first longitudinal member 12. The wires 17(1) and 17(2) deliver radiofrequency energy from the radiofrequency energy source 16 to provide radiofrequency energy to the body region, although other energy sources configured to supply other energy modalities may be employed.

Figure 6:
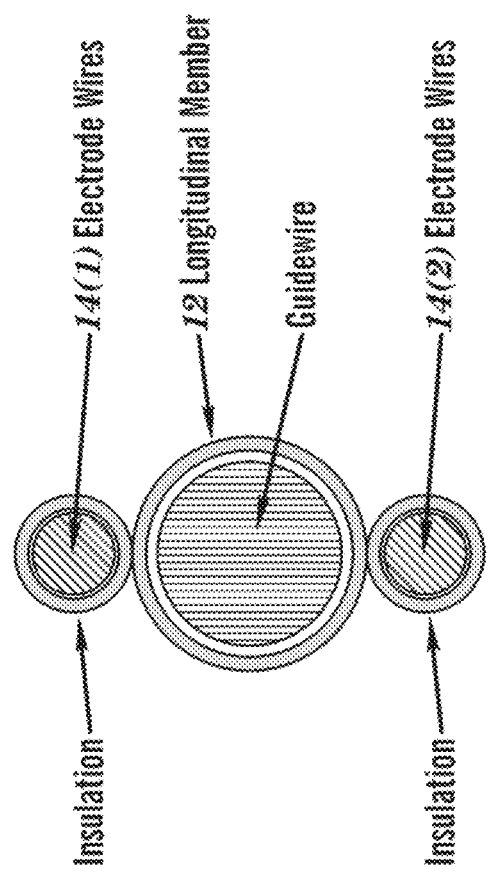
FIG. 6 is a schematic end view of the longitudinal member of FIG. with two coupled, insulated electrodes.

Referring now to FIG. 6, the electrodes 14(1) and 14(2) are insulated, such as with a dielectric barrier, such that the two electrodes 14(1) and 14(2) are capable of generating an electric field in the body region. Further, the insulation is selected to allow the electrodes 14(1) and 14(2) to be capable of withstanding the generation of a plasma discharge around the electrodes 14(1) and 14(2). The electrodes 14(1) and 14(2) may further have a dielectric barrier located at an exposed portion of the electrodes 14(1) and 14(2) to further aid in withstanding plasma generation.

Referring again more specifically to FIGS. 1 and 5, the radiofrequency energy source 16 provides a source of radiofrequency energy that is delivered to the body region through electrodes 14(1) and 14(2), although other energy modalities may be employed. In one example, the radiofrequency energy source 16 provides modulated pulses of radiofrequency energy to the electrodes 14(1) and 14(2). In one example, the radiofrequency energy source 16 is configured to provide modulated pulses having a pulse width between about 0.05 to about 500 microseconds, although modulated pulses having a pulse width of less than 0.05 microseconds or between 500 microseconds and 1 second may be employed. The radiofrequency energy source 16 may further be configured to provide the modulated pulses in packets. Each packet of modulated pulses may have between 2 and 10 pulses, by way of example only. In another example, the modulated pulses are grouped into bursts having a burst width between 100 ms to 1 s and an interval between each burst between 1 ms to 100 ms, by way of example only.

The radiofrequency energy source 16 provides radiofrequency energy at a voltage between 400V to 4000V, although voltages less than 400V may be utilized in some examples. The radiofrequency energy source 16 is capable of providing radiofrequency energy at a level that produces a delivery condition in the body region that enhances delivery of the composition, such as cavitation, microjets, shockwaves, electrical stimulation, or a chemical reaction. In one example, the radiofrequency energy source 16 provides energy to generate shockwaves having an instantaneous magnitude between 0.1 MPa to 20 MPa. In another example, the radiofrequency energy source 16 provides energy to generate one or more regions of cavitation bubbles in the body region having a diameter between 1 μm and 10 mm. The cavitation bubbles may be formed from the composition delivered to the body region using the composition delivery device 10.

Referring again to FIGS. 1 and 5 more specifically, the composition delivery device 10 further includes the composition delivery element 18 located at the distal end 22 of the first longitudinal member 12. The composition delivery element 18 includes a composition layer 24 of the composition to be delivered to the body region located on a surface 25 of the composition delivery element 18. The composition layer 24 is coated on and/or imbedded within the surface 25 of the composition delivery element 18. Methods of applying the composition layer 24 can include spraying, dip coating, vapor deposition, plasma deposition, using a chemical bond, or using an electrical bond, by way of example only.

Figure 10:
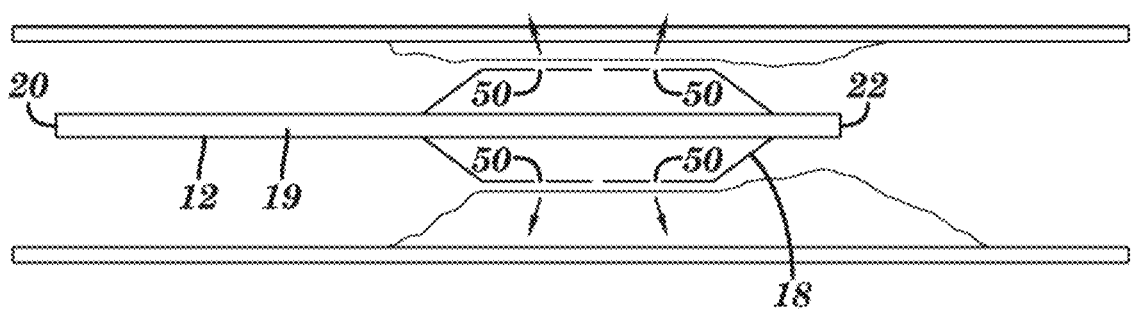
FIG. 10 illustrates a schematic of another exemplary composition delivery device with a composition delivery element with a porous surface.

In another example the composition, rather than being placed on the outside of the composition delivery element, is injected inside the composition delivery element 18. The composition delivery element 18 includes pores 50 that allow the composition to escape through the pores 50 and be delivered into the body region, such as an occlusion or vessel wall as shown in FIG. 10. This delivery of the composition is enhanced by activation of radiofrequency energy as described further below. In another example the composition is located on the composition delivery element as a charged compound. The radiofrequency energy is then delivered with a similar charge so the composition is repelled from the composition delivery element 18 and into the tissue. Additionally or alternatively, an electrically neutral therapeutic agent may be modified by adding a charged moiety such that the modified therapeutic agent comprising the charged moiety may be more susceptible to the influence of the energy field. Additionally, the therapeutic agent may be submerged or dissolved in a conductive fluid, whereby the conductive fluid path under the influence of the energy field as described above serves as a vehicle to facilitate the delivery of the therapeutic agent to the treatment region. By way of example, drugs to treat anemia may be used.

The composition is a therapeutic agent or a pharmaceutical compound. Non-limiting examples of the compositions that may be utilized with the composition delivery device include a thrombolytic agent, a fibrinolytic enzyme, a thrombin inhibitor, an antiplatelet agent, an anticoagulant, an anti-restenotic agent, or an anti-cancer agent, although other therapeutic agents or pharmaceutical compounds may be delivered using the composition delivery device 10. The composition can be a drug, gas, or liquid which can have an effect on the targeted body region. As an example, the composition could be Paclitaxel or a drug taken from the limus family of drugs and used to be delivered to the vessel body of an occlusion to reduce the likelihood of such vessel from reoccluding or restenosing.

It is contemplated that the present embodiments may be used to deliver other therapeutic agents or other biologically active substances including but not limited to: amino acids, anabolics, analgesics and antagonists, anesthetics, anthelmintics, anti-adrenergic agents, anti-asthmatics, anti-atherosclerotics, antibacterials, anticholesterolics, anti-coagulants, antidepressants, antidotes, anti-emetics, anti-epileptic drugs, ant-fibrinolytics, anti-inflammatory agents, antihypertensives, antimetabolites, antimigraine agents, antimycotics, antinauseants, antineoplastics, anti-obesity agents, anti-Parkinson agents, antiprotozoals, antipsychotics, antirheumatics, antiseptics, antivertigo agents, antivirals, bacterial vaccines, bioflavonoids, calcium channel blockers, capillary stabilizing agents, coagulants, corticosteroids, detoxifying agents for cytostatic treatment, contrast agents (like contrast media, radioisotopes, and other diagnostic agents), electrolytes, enzymes, enzyme inhibitors, gangliosides and ganglioside derivatives, hemostatics, hormones, hormone antagonists, hypnotics, immunomodulators, immunostimulants, immunosuppressants, minerals, muscle relaxants, neuromodulators, neurotransmitters and nootropics, osmotic diuretics, parasympatholytics, para-sympathomimetics, peptides, proteins, respiratory stimulants, smooth muscle relaxants, sympatholytics, sympathomimetics, vasodilators, vasoprotectives, vectors for gentherapy, viral vaccines, viruses, vitamins, and the like.

Figure 7:
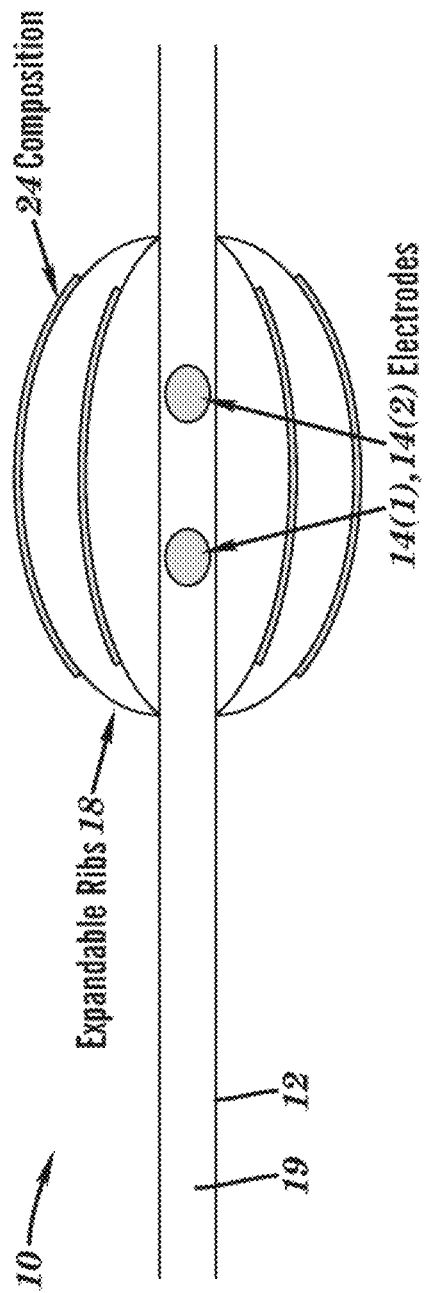
FIG. 7 is a schematic of an exemplary device for composition delivery with another exemplary composition delivery element.

In this example, the composition delivery element 18 is an expandable balloon having a porous surface 25 to which the composition layer 24 is applied, although other composition delivery elements, such as an expandable catheter, or a stent may be utilized. In another example, the composition delivery element 18 may be microbubbles filled with the composition that are delivered to the body region through the lumen 19 of the first longitudinal member 12, by way of example. In another example, as shown in FIG. 7, the composition delivery element 18 comprises a plurality of expandable ribs with the composition located thereon.

Figure 8:
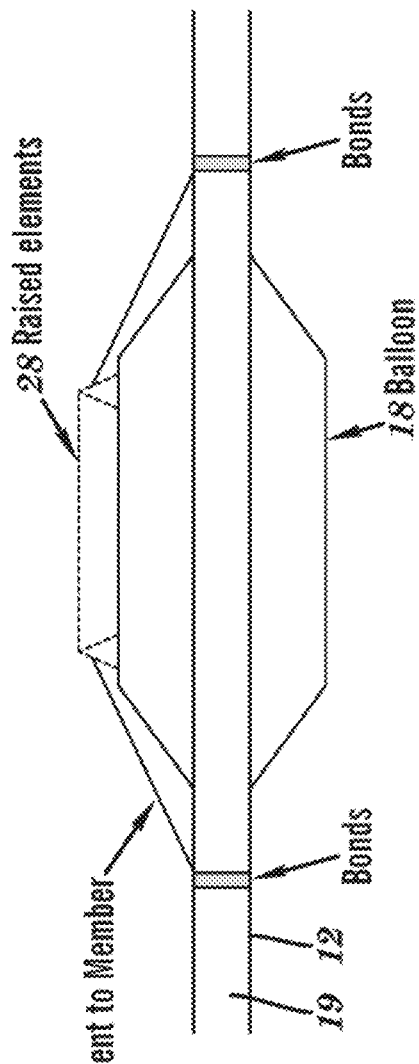
FIG. 8 is a schematic of a configuration for securing an exemplary raised element to an exemplary composition delivery element that may be employed with the composition delivery device of the present technology.

Referring now again more specifically to FIGS. 1 and 5, the composition delivery element 18, such as a balloon, includes one or more raised elements 28 located on the surface 25 thereof. The raised elements 28 are configured to simultaneously score or cut the body region, such as an occlusion, so that a composition can more readily diffuse into the area into which the composition delivery element 18 is inserted. The raised elements 28 may comprise longitudinal or circumferential elements located on the composition delivery element 18. In one example, the raised elements 28 have a triangular cross section, although other configurations may be utilized. The raised elements 28 are constructed of a metal or a polymer, by way of example, although other materials may be utilized. The composition layer 24 may be applied directly to the raised elements 28 of the composition delivery element 18. In this example, the raised elements 28 are coupled directly to the composition delivery element 18. Alternatively, referring now to FIG. 8, the raised elements 28 may be coupled directly to the first longitudinal member 12, although other configurations may be utilized.

An example of a method for enhanced delivery of a composition to a body region of a patient utilizing radiofrequency energy will now be described with reference to FIGS. 1-8. First, the longitudinal member 12 including the composition delivery element 18 with the composition layer 24 located on the surface 25 is delivered to the body region of the patient to be treated. The body region may be various regions in the body such as organs, body lumens or cavities, such as various ducts or vessels, blood vessels, grafts, glands. In one example, the body region may be an area in the body including an occlusion or a tumor that requires treatment. The composition layer 24 may be coated or imbedded on the surface 25 of the composition delivery element 18, although in other examples the composition layer 24 may be located on the raised elements protruding from the surface 25 of the composition delivery element 18, such as an expandable balloon.

Once located in the body region, the composition delivery element 18 may be expanded to apply the composition layer 24 to the body region. The composition is a therapeutic agent or a pharmaceutical compound. Non-limiting examples of the compositions that may be utilized with the composition delivery device include a thrombolytic agent, a fibrinolytic enzyme, a thrombin inhibitor, an antiplatelet agent, an anticoagulant, an anti-restenotic agent, or an anti-cancer agent, although other therapeutic agents or pharmaceutical compounds may be delivered using the composition delivery device 10.

Next, the first electrode 14(1) and the second electrode 14(2) coupled to the radiofrequency energy source 16 are directed to the location proximate to the body region. In one example, the longitudinal member 12 has electrodes 14(1) and 14(2) located thereon, as shown in FIGS. 1 and 5, such that the electrodes 14(1) and 14(2) are delivered simultaneously with the longitudinal member 12.

In another example, as shown in FIG. 2, the electrodes 14(1) and 14(2) are delivered on second longitudinal member 13 that is configured to be inserted into the lumen 19 of the first longitudinal member 12 to be delivered proximate to the body region of the patient. In this example, the electrodes 14(1) and 14(2) are directed to the body region after delivery of the composition delivery element 18.

In yet another example, as shown in FIG. 3, the electrodes 14(1) and 14(2) are directed separately to the body region through the lumen 19 of the first longitudinal member 12 on the second longitudinal member 13 and the third longitudinal member 23, which are independent, non-overlapping guidewires or catheters, respectively. In this example, the second longitudinal member 13 and the third longitudinal member 23 may be delivered to the body in the same direction or in opposition directions, using an antegrade/retrograde approach, as described in U.S. Pat. No. 9,561,073, the disclosure of which is incorporated herein by reference in its entirety.

As disclosed in U.S. Pat. No. 7,918,859 by the same inventors, which is incorporated herein in its entirety, in the controlled antegrade and retrograde tracking (CART) technique the retrograde approach takes advantage of an intercoronary channel. Such a channel may be an epicardial channel, an inter-atrial channel, an intra-septal channel (also referred to as septal collateral), or a bypass graft. The basic concept of the CART technique is to create a channel through an occlusion, preferably with limited dissections, by approaching the occlusion both antegradely and retrogradely.

In a further example, a patch including one of the electrodes 14(1) or 14(2) is placed on the patient's skin proximate the body region of the patient to be treated. The patch is placed in close proximity to the body region to allow for the bipolar arrangement between the electrodes 14(1) and 14(2).

Next, radiofrequency energy is delivered from the radiofrequency energy source 16 to the electrodes 14(1) and 14(2) in modulated pulses. In one example, the radiofrequency energy source 16 provides modulated pulses having a pulse width between about 0.05 to about 500 microseconds, although modulated pulses having a pulse width of less than 0.05 microseconds or between 500 microseconds and 1 second may be employed. The radiofrequency energy source 16 may further provide the modulated pulses in packets having between 2 and 10 pulses, by way of example only. In another example, the modulated pulses are grouped into bursts having a burst width between 100 ms to 1 s and an interval between each burst between 1 ms to 100 ms, by way of example only.

The delivery of the modulated pulses may be gated using an electrocardiogram (ECG) or another waveform signal obtained from the body of the patient. In one example, a third patch containing an electrode may be placed outside of the body region and electrically coupled to the electrodes 14(1) and 14(2). In yet another example, a third electrode may be located near the body region in order measure impedance based on the delivery of the radio frequency energy. The impedance measurements may then be utilized to optimize the delivery of the radiofrequency energy.

The radiofrequency energy source 16 provides the radiofrequency energy at a voltage between 400V to 4000V, although voltages less than 400V may be utilized in some examples. In one example, the incident intensity of the radiofrequency energy in the body region is between about 0.1 Joules to 5 Joules per square millimeter. In one example, the radiofrequency energy is delivered until an electrical limit, such as 100 Ohms, is met, although other electrical limits may be employed.

The radiofrequency energy source 16 provides radiofrequency energy at a level that produces a delivery condition in the body region that enhances delivery of the composition, such as cavitation, microjets, shockwaves, electrical stimulation, or a chemical reaction. In one example, the radiofrequency energy source 16 provides energy to generate shockwaves having an instantaneous magnitude between 0.1 MPa to 20 MPa. In another example, the radiofrequency energy source 16 provides energy to generate one or more regions of cavitation bubbles in the body region having a diameter between 1 μm and 10 mm. The cavitation bubbles may be formed from the composition delivered to the body region using the composition delivery device 10.

The delivery of radiofrequency energy provides for prolonged delivery of the composition and imbedding of the composition within the body region to provide enhanced treatment. The radiofrequency signal can be adjusted using a number of modifications to the pulse such as by shortening or lengthening the pulse duration or adjusting the pulse period. As an example, by shortening the pulse duration to the micro or nanosecond range, a stronger mechanical effect can be obtained inducing stronger mechanical effects (i.e. deeper injection or imbedding) of the composition into the body region. A deeper imbedding of the composition is likely to result in a longer duration of the composition within the body region enabling a more durable effect from the composition.

By way of example, the delivery of radiofrequency energy may be utilized to provide a mechanical force that enhances diffusion of the composition into the body region. Alternatively, the radiofrequency energy may be employed to cause impacts on the body region itself, such as vasodilation, increased cell permeability, or reversible electroporation that increase the effectiveness of the delivery of the composition to the body region.

By way of example, the method may be utilized to treat on occlusion. The radiofrequency energy is applied between the two electrodes 14(1) and 14(2) generating a plasma and modifying the surrounding plaque or occlusion or vessel wall utilizing the effects of the plasma generation, such as cavitation or shockwaves. The composition is delivered to the occlusion, which has now become more amenable to diffusion or delivery of the composition due to the effects of the plasma generation, thus enhancing the delivery of the composition into the vessel wall. The delivery of the radiofrequency energy to the vessel wall or occlusion can induce vasodilation, alter cell permeability, or electroporation or the like to enhance the delivery of the composition. By adjusting the radiofrequency signal, the composition can be delivered deeper into the vessel wall, thus allowing the composition to remain within the vessel wall for a prolonged period of time and improving the durability of the composition within the vasculature.

In another example, the electrodes 14(1) and 14(2) are placed on the same device as the composition, which allows for simultaneous modification of the surrounding tissue and delivery of radiofrequency energy to enhance delivery of the composition. In this example, the composition delivery element 18, such as a balloon catheter, has the composition layer 24 placed on the outside surface 25 of the balloon. The electrodes 14(1) and 14(2) are located inside the composition delivery element 18 as either an attachment to the first longitudinal member 12 as shown in FIG. 1, or delivered through the lumen 19 of the first longitudinal member 12 as shown in FIGS. 2 and 3. The radiofrequency energy is then delivered and the effects of the radiofrequency energy are transmitted through the composition delivery element 18, such as a balloon, to the composition layer 24 and the vessel wall enhancing delivery of the composition to the vessel wall.

Figure 9A:
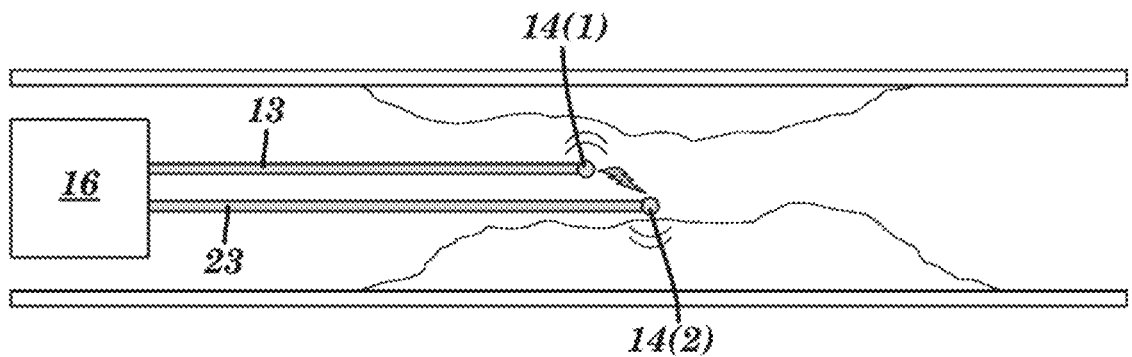
FIGS. 9A-9C illustrates an exemplary method for enhanced composition delivery using radiofrequency energy.
Figure 9B:
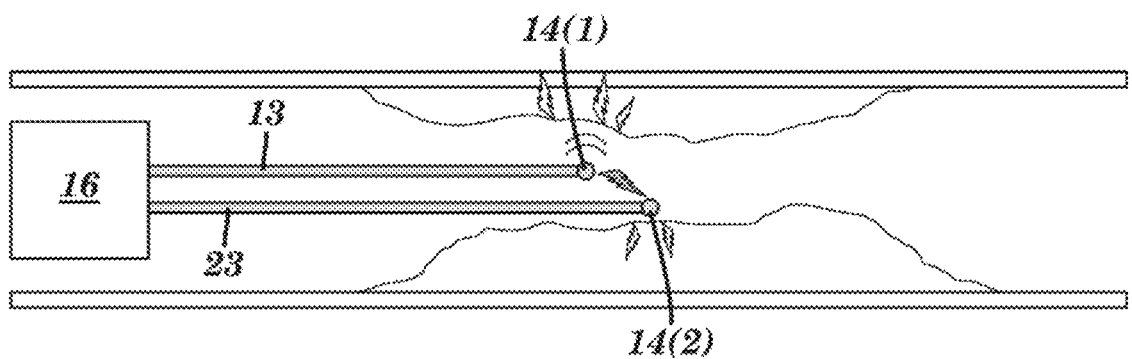

Another exemplary method for enhanced delivery of a composition to a body region of a patient, such as an occlusion, utilizing radiofrequency energy will now be described with reference to FIGS. 9A-9C. In this example, electrodes 14(1) and 14(2) are directed to the occluded area in the vessel on the second longitudinal member 13 and the third longitudinal member 23 prior to delivery of the composition to the body area, as shown in FIG. 9A.

Radiofrequency energy is then applied as set forth above. The application of radiofrequency energy generates a plasma and modifies the surrounding plaque or occlusion or vessel wall utilizing the effects of the plasma generation, such as cavitation or shockwaves, as shown in FIG. 9B. The electrodes 14(1) and 14(2) are then removed from the body region.

Figure 9C:
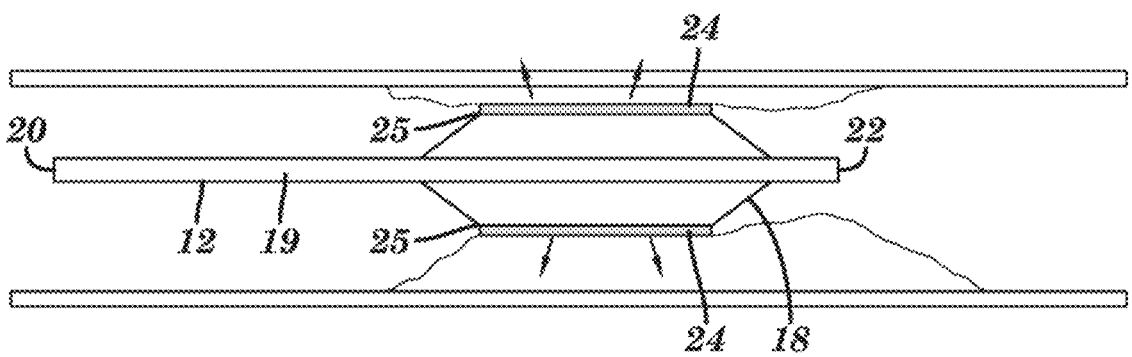

Next, the composition is delivered to the occlusion using composition delivery element 18 as shown in FIG. 9C. The occlusion has become more amenable to diffusion or delivery of the composition due to the effects of the plasma generation, thus enhancing the delivery of the composition into the vessel wall. The delivery of the radiofrequency energy to the vessel wall or occlusion can induce vasodilation, alter cell permeability, or electroporation or the like to enhance the delivery of the composition. By adjusting the radiofrequency signal, the composition can be delivered deeper into the vessel wall, thus allowing the composition to remain within the vessel wall for a prolonged period of time and improving the durability of the composition within the vasculature.

Example

Figure 11:
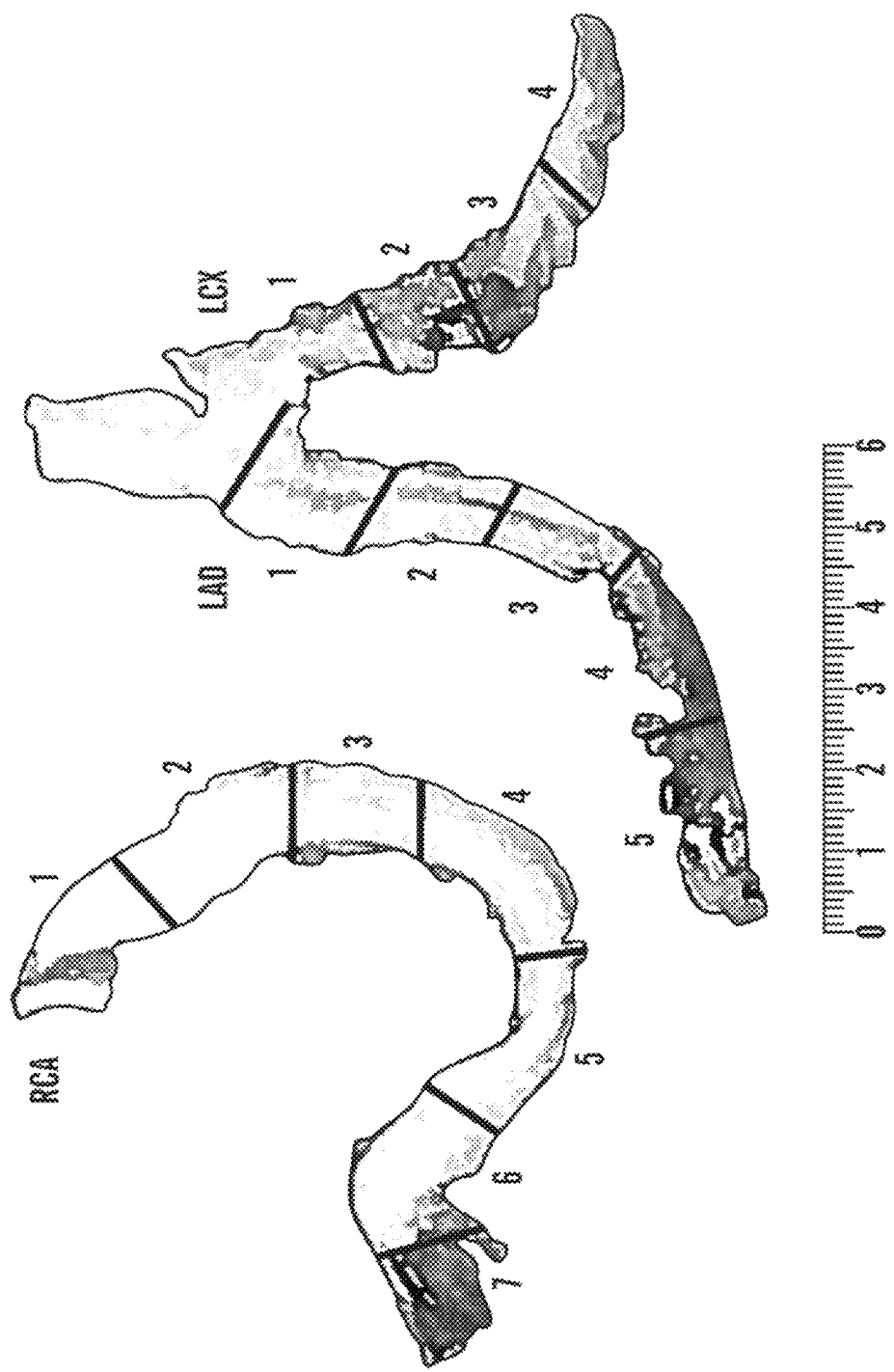
FIG. 11 illustrates the effect of plasma-mediated ablation using radiofrequency energy within a nonoccluded vessel.

Preclinical work (FIG. 11) has shown that at very high voltages, the effect of plasma-mediated ablation using radiofrequency energy within a nonoccluded vessel can result in effects that propagate into the vessel wall. In particular, medial dissections and/or hemorrhaging perivascularly can occur into the outer vessel wall. However, by altering the radiofrequency delivery settings, these effects can be controlled such that they enhance delivery of a composition into the vessel wall or occlusion without creating deleterious effects. Examples of alterations can include reducing the voltage or current levels, modifying the pulse period, modifying the pulse duration, or modifying the number of pulses delivered during radiofrequency delivery.

As an example, in the case of an occlusion in a vessel wall, it has been shown that the use of voltages in the range of 1200V to 2000V can ablate tissue and create a channel through the occlusion in a very short period of time. The delivery of drugs or other compositions would likely require less energy or a lower voltage as the objective is not to create a channel but to enhance the delivery of the drug into the vessel wall. Similarly, it has been shown that very short pulses (on the order of nano seconds) generally create larger mechanical forces (e.g. shockwaves) than longer pulses. It would be preferred to deliver enough mechanical force to enhance delivery of the drug or composition into the vessel wall without causing damage to the wall itself.

Accordingly, as illustrated and described by way of the examples herein this technology provides more efficient and effective devices and methods for delivering a composition to a body region. The devices and methods of this technology allow the composition to remain within the body region site for an extended period of time to provide enhanced treatment. In particular, the use of cavitation, shockwaves, electroporation, or the like, generated by radiofrequency energy or other energy source aids in the delivery of the composition. This technology also advantageously provides an enhanced method for delivering a drug into a vessel wall or occlusion such that the drug remains within the targeted site for a longer period of time without leaving anything behind. Prolonged action of the drug within the targeted site can lead to improved outcomes (e.g. reduced reocclusion, restenosis, or revascularization rates)

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A device for enhanced delivery of a composition to a body region of a patient utilizing radiofrequency energy, the device comprising:
    a first longitudinal member with a proximal end and a distal end with at least one lumen extending between the proximal end and the distal end;
    a composition delivery device located at the distal end of the longitudinal member, the composition delivery device having the composition located on an outside surface thereof; and
    at least two electrodes located on the first longitudinal member to be located within the composition delivery device, the at least two electrodes coupled to a radiofrequency source to receive radiofrequency energy from the radiofrequency source and insulated such that they can generate an electric field to enhance delivery of the composition to the body region, wherein the radiofrequency energy is delivered from the radiofrequency source to the at least two electrodes in modulated pulses and the delivery of modulated pulses is gated based on a waveform signal obtained from a body of a patient.

2. The device of claim 1, wherein the composition delivery device comprises a balloon.

3. The device of claim 2, wherein the balloon has a porous surface.

4. The device of claim 1, wherein the at least two electrodes are balloon markers.

5. The device of claim 1, wherein the composition is a therapeutic agent or a pharmaceutical compound.

6. The device of claim 5, wherein the therapeutic agent or pharmaceutical compound is a thrombolytic agent, a fibrinolytic enzyme, a thrombin inhibitor, an antiplatelet agent, an anticoagulant, an anti-restenotic agent, or an anti-cancer agent.

* * * * *